United States Patent
Field et al.

(10) Patent No.: US 8,298,193 B2
(45) Date of Patent: Oct. 30, 2012

(54) PLUNGER ROD HEAD FOR ACTIVATING NEEDLE SAFETY DEVICE

(75) Inventors: Frederic P. Field, San Diego, CA (US); Philip Dowds, San Diego, CA (US); James M. Verespej, San Marcos, CA (US)

(73) Assignee: Safety Syringes, Inc., Carlsbad, CA (US)

(*) Notice: Subject to any disclaimer, the term of this patent is extended or adjusted under 35 U.S.C. 154(b) by 0 days.

(21) Appl. No.: 12/707,080

(22) Filed: Feb. 17, 2010

(65) Prior Publication Data

US 2010/0217204 A1    Aug. 26, 2010

Related U.S. Application Data

(60) Provisional application No. 61/153,165, filed on Feb. 17, 2009.

(51) Int. Cl.
*A61M 5/32* (2006.01)
(52) U.S. Cl. ...................................................... 604/198
(58) Field of Classification Search .......... 604/192–198, 604/110, 187
See application file for complete search history.

(56) References Cited

U.S. PATENT DOCUMENTS

| 5,137,521 | A | 8/1992 | Wilkins | |
| 5,718,239 | A | 2/1998 | Newby et al. | |
| 5,893,845 | A | 4/1999 | Newby et al. | |
| 7,300,420 | B2* | 11/2007 | Doyle | 604/192 |
| 2006/0095010 | A1* | 5/2006 | Westbye | 604/197 |

OTHER PUBLICATIONS

WO, PCT/US2010/024506—Search Report, Apr. 28, 2010.

* cited by examiner

*Primary Examiner* — Kevin C Sirmons
*Assistant Examiner* — Imani Hayman
(74) *Attorney, Agent, or Firm* — Dickstein Shapiro LLP; Kenneth S. Roberts

(57) ABSTRACT

A passive needle safety device for protecting the needle of an injection syringe after medication has been delivered to a patient comprising a body that can hold a syringe, a telescoping guard fitting over the body, and a spring deployed between the guard and body such that the guard is urged in an extend configuration distally relative to the body, the improvement comprising, trigger fingers for holding the guard and body together in an un-extended configuration against the force of the spring, and a plunger rod with a plunger head which pushes against the trigger fingers, the head having an angled surface that provides a lateral component of force to the trigger fingers to displace them from the latched configuration to an unlatched configuration.

5 Claims, 3 Drawing Sheets

PLUNGER ROD HEAD FOR ACTIVATING NEEDLE SAFETY DEVICE

This application is based on U.S. Provisional application Ser. No. 61/153,165 filed Feb. 17, 2009, which is fully incorporated herein by reference.

The present invention relates to an improved plunger rod used with a syringe as part of a passive needle safety device. Such a safety device protects the needle of an injection syringe after the medication has been delivered. The safety device itself consists of a body that holds the syringe and a telescoping guard that fits over the body. A spring is deployed between these two components such that the guard and body are urged in an extended configuration causing the guard to move distally relative to the body and syringe or, if the guard is stationary (e.g. against the patient's skin), the body is pushed proximally pulling the needle into the guard where it is protected from contacting healthcare providers.

Figure 1:
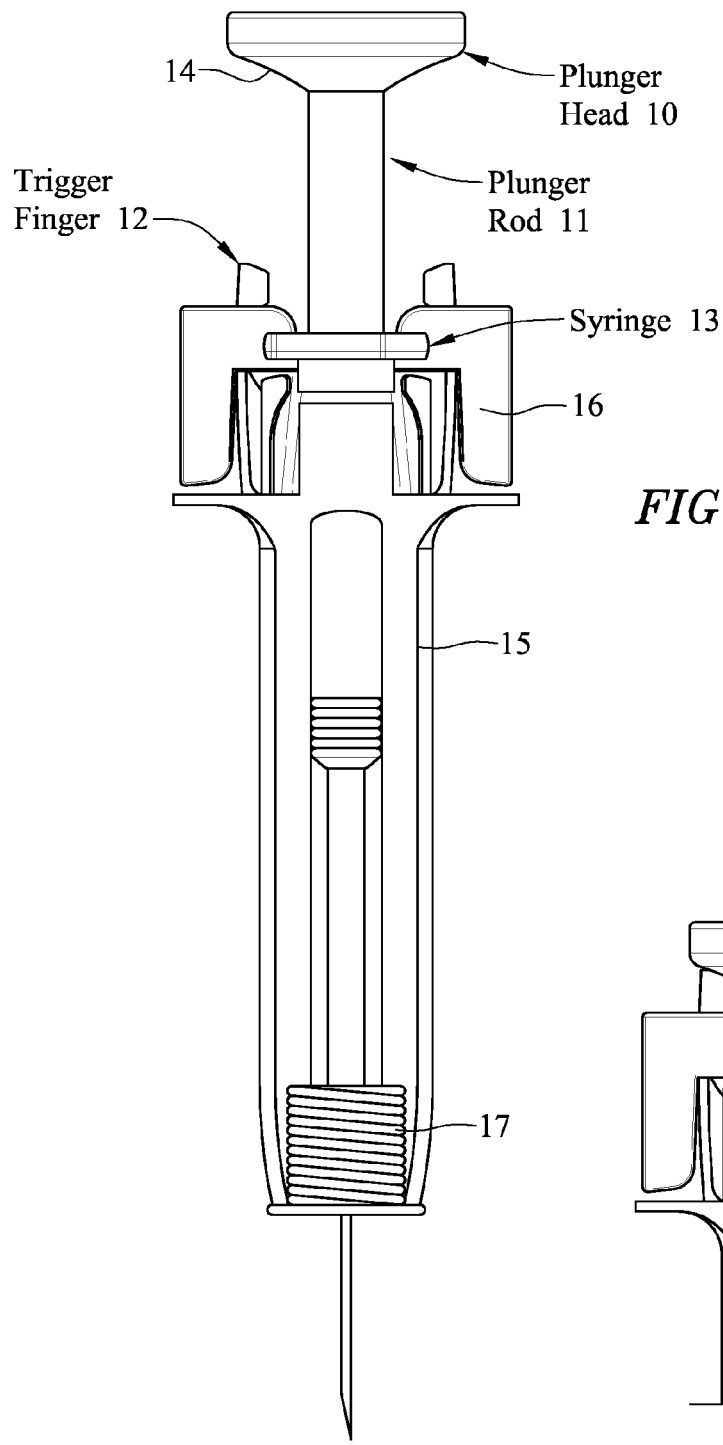
FIG. 1 shows the configuration of a plunger rod with respect to trigger fingers prior to an injection.
Figure 2:
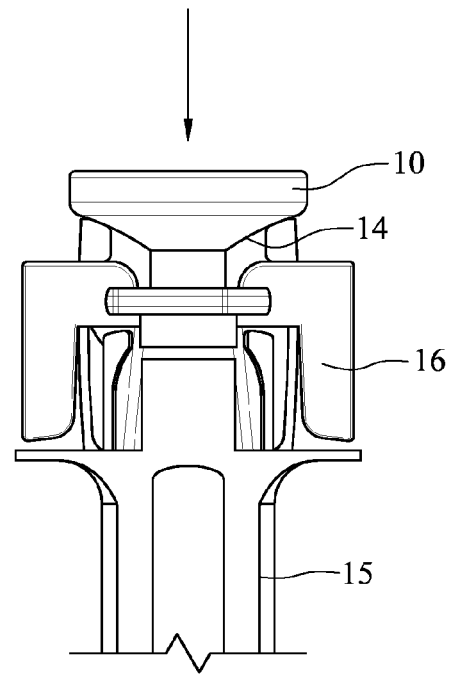
FIG. 2 shows as the plunger rod is depressed in the direction of the arrow, a plunger head and trigger fingers will come into contact.
Figure 3:
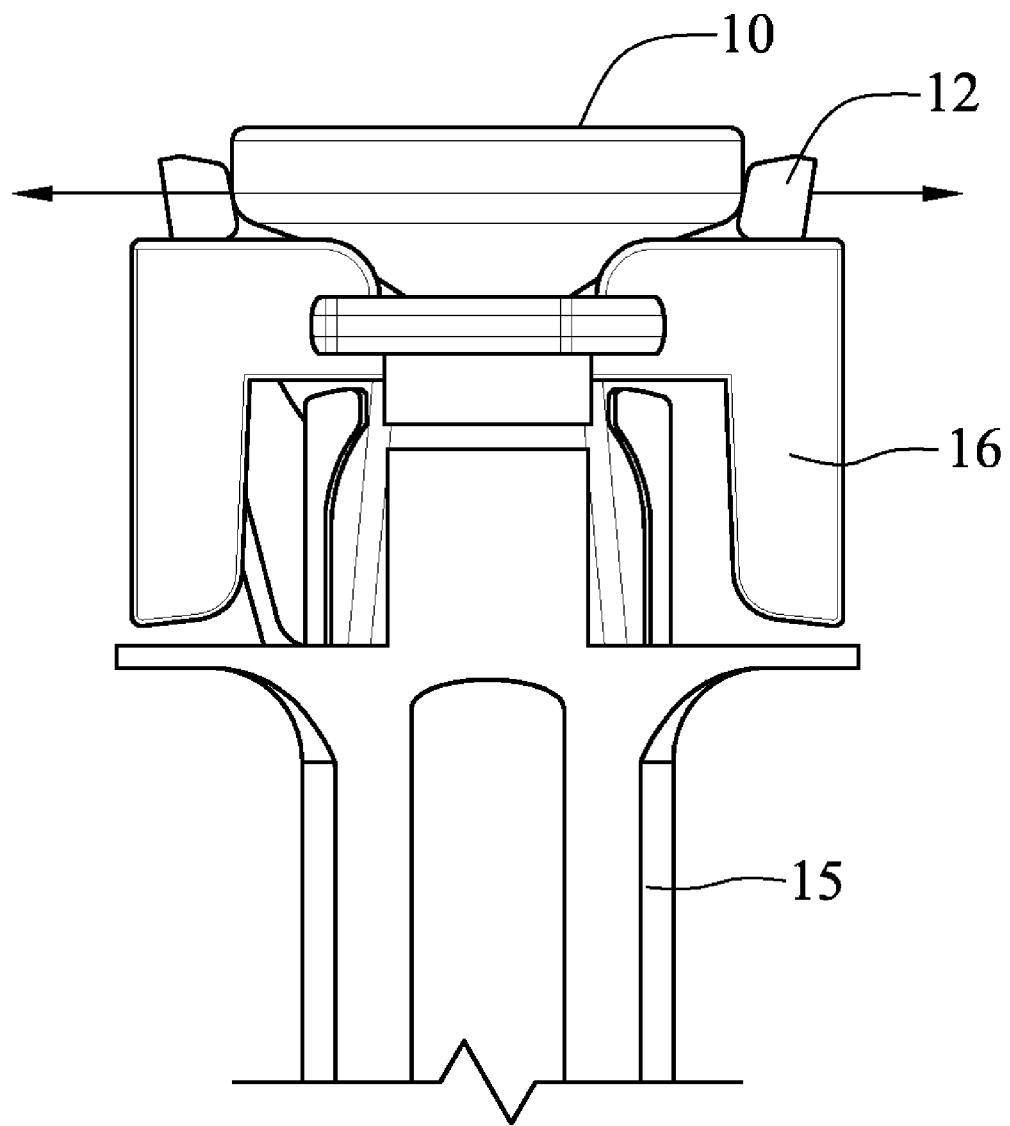
FIG. 3 shows as the plunger rod continues into the syringe, trigger fingers move in a lateral direction as indicated by the arrows, and shortly thereafter the stopper at the end of the plunger rod bottoms out at the end of the syringes.

The present invention relates to safety devices that are known as passive devices in that the needle guard is activated or deployed automatically at the end of injection. An example is shown in U.S. Pat. No. 7,300,420. Deployment of the safety device over the needle is initiated when the plunger rod head 10 displaces trigger fingers 12 (see FIGS. 1, 2, and 3 herein) near the end of injection from a latched position that holds the guard 15 and body 16 together in an un-extended configuration against the force of a spring 17. With the trigger fingers 12 unlatched, the spring 17 urges the relative movement of the guard 15 and body 16 to the needle-protected configuration.

During unlatching of the trigger fingers 12, the plunger head 10 pushes against the trigger fingers using an angled or cam surface 14 that provides a lateral component of force to the trigger fingers to displace them from the latched configuration to the unlatched configuration. The magnitude of the lateral force is dictated by the angle of the plunger head surface with respect to the perpendicular direction of travel of the plunger rod 11. The larger the angle, the higher the lateral force against the trigger fingers, but the slower the lateral displacement of the trigger fingers per unit forward travel of the plunger rod. Unlatching of the trigger fingers occurs when the trigger fingers have been moved laterally a certain distance by a force sufficient to do so. In order for this to happen, the lateral force must exceed the frictional force preventing the trigger fingers from sliding on the plunger head surface. The frictional force is dictated by the normal force and the coefficient of friction between the plunger head 10 and the trigger fingers 12. To push the trigger fingers the required lateral distance to unlatch them, the plunger head must continue to present its angled surface 14 to the trigger fingers until sufficient lateral movement is obtained.

If the trigger fingers are unlatched too early during the injection of medication, the safety device may push against the patient to an extent that the needle is pulled out of the patient before the entire dose of medication is delivered. Thus, there is a desire to unlatch the trigger fingers and activate the guard mechanism just before the end of injection. Therefore activation must happen with as little forward movement of the plunger rod 11 as possible, but before the plunger rod has pushed the stopper to the end of the syringe. To do so requires a small angle of the plunger head 10 with respect to the perpendicular direction of travel so that the lateral displacement of the trigger fingers 12 is highest per unit forward movement of the plunger rod, yet high enough that the lateral force exceeds the frictional drag between the trigger fingers and the plunger head. The frictional force can be minimized by using dissimilar materials in the trigger fingers 12 and the plunger head 10. For example, polycarbonate can be used for the trigger fingers and polypropylene or polyethylene for the plunger head.

Figure 4A:
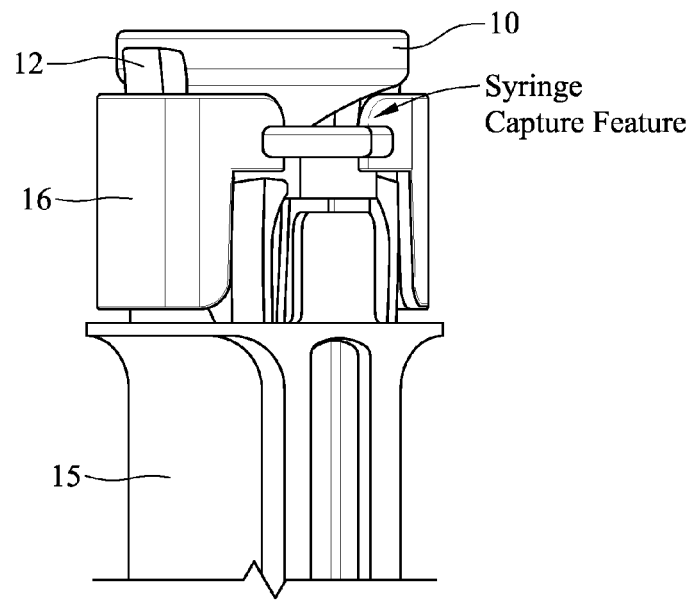
FIGS. 4a and 4b illustrate in FIG. 4a the improved plunger head geometry showing clearance with surrounding structures and an angled surface that is constant. The standard plunger rod shown in FIG. 4b shows an angled surface that is curved so that lateral displacement of the trigger fingers is less the further the plunger rod is pressed, causing the stopper to bottom out in the syringe before complete unlatching or requiring unlatching significantly before the end of the injection.
Figure 4B:
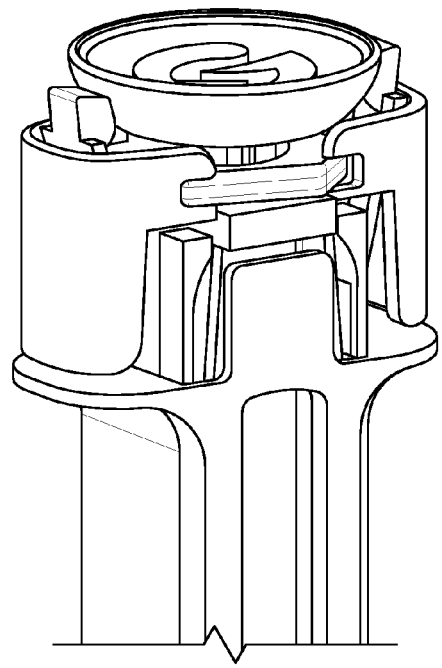

Rapid lateral displacement of the latch fingers occurs with a plunger rod head having an angled surface that is a constant angle as opposed to the many existing plunger rod heads that have a curved surface such that the angle becomes greater as the plunger is pressed further forward causing the lateral displacement of the trigger fingers to slow down (see FIG. 4a). Thus the constant angle plunger head surface achieves activation sooner and can allow the activation of the guard mechanism to take place closer to the end of injection. Of course the plunger head 10 geometry must clear the surrounding structures of the safety device and geometric tolerances of the syringe and the stopper must be taken into account such that unlatching of the trigger fingers always occurs before the plunger rod is prevented from moving further forward.

A final requirement is that the force to push the plunger rod forward 11 to unlatch the trigger fingers 12 must not be so great as to give the user the false impression that they have pushed the stopper to the end of the syringe and that all the medication has been delivered. Many competitive devices require substantial force to activate the device resulting in many users not ever experiencing or realizing the safety activation.

Our testing has indicated that if the trigger finger material is polycarbonate and the plunger head material is polypropylene, that a plunger head angled surface of 10 degrees does not reliably push the trigger fingers laterally (not enough lateral force component compared to the frictional force) resulting in no activation of the device. An angled surface of 15 degrees displaces the trigger fingers laterally for activation, but occasionally requires high plunger rod forces. An angled surface of 20 degrees achieves consistent activation or unlatching of the trigger fingers with a low and consistent plunger rod force. Thus, we feel that the above arrangement of components with the 20 degree angled plunger rod surface gives the fastest last-minute activation, but with the lowest and most consistent plunger rod forces.

While the invention is susceptible to various modifications, and alternative forms, specific examples thereof have been herein described in detail. It should be understood, however, that the invention is not to be limited to the particular forms or methods disclosed, but to the contrary, the intention is to cover all modifications, equivalents, and alternatives falling within the spirit and scope of the appended claims.

What is claimed is:

1. A passive needle safety device for protecting the needle of an injection syringe after medication has been delivered to a patient comprising
- a body that can hold a syringe,
- a telescoping guard fitting, over the body, and
- a spring deployed between the guard and body such that the guard is urged in an extended configuration distally relative to the body, the improvement comprising,
- trigger fingers for holding the guard and body together in an un-extended configuration against the force of the spring, and a plunger rod with a plunger head which pushes against the trigger fingers, the plunger head having an angled surface that provides a lateral component of force to the trigger fingers to displace them from the latched configuration to an unlatched configuration, wherein the angled surface of the plunger head extends from a lateral edge of the plunger head to the plunger rod at a constant angle of and is approximately 20° so as to provide consistent activation of the trigger fingers with a low and constant plunger rod force.

2. The needle safety device of claim 1, wherein the plunger head and the trigger fingers are made of different materials.

3. The needle safety device of claim 1, wherein the trigger fingers are made of polycarbonate.

4. The needle safety device of claim 3, wherein the plunger head is made of polypropylene.

5. The needle safety device of claim 3, wherein the plunger head is made of polyethylene.

* * * * *